United States Patent [19]

Zeitlin et al.

[11] Patent Number: 5,095,146
[45] Date of Patent: Mar. 10, 1992

[54] WATER ADDITION TO CRYSTALLIZATION TRAIN TO PURIFY TEREPHTHALIC ACID PRODUCT

[75] Inventors: Martin A. Zeitlin, Naperville; Diane Wilger-Nowicki, St. Charles, both of Ill.

[73] Assignee: Amoco Corporation, Chicago, Ill.

[21] Appl. No.: 674,783

[22] Filed: Mar. 25, 1991

[51] Int. Cl.$^5$ .............................................. C07C 51/43
[52] U.S. Cl. ...................................... 562/486; 562/485
[58] Field of Search .............................. 562/486, 485

[56] References Cited

U.S. PATENT DOCUMENTS 3,944,602 3/1976 Katzschmann ................... 562/485
4,357,475 11/1982 Hanotier et al. .................. 562/414

Primary Examiner—Jose G. Dees
Assistant Examiner—Vera C. Clarke
Attorney, Agent, or Firm—Gunar J. Blumberg; William H. Magidson; Ralph H. Medhurst

[57] ABSTRACT

Optical density of terephthalic acid is reduced in excess of ninety percent by the direct addition of water to selected crystallizers in a precipitative process based on hydrogenation and flask crystallization.

12 Claims, No Drawings

WATER ADDITION TO CRYSTALLIZATION TRAIN TO PURIFY TEREPHTHALIC ACID PRODUCT

BACKGROUND OF THE INVENTION

1. Field of the Invention

The present invention relates to a process for the production of an aromatic polycarboxylic acid. More particularly, it relates to a process for reducing the optical density of terephthalic acid product comprising a liquid aqueous solution substantially saturated with terephthalic acid and comprising about 500 parts per million (p.p.m.) to about 6,000 p.p.m. of p-toluic acid at a temperature of about 204° C. (400° F.) to about 288° C. (550° F.).

2. Description of the Prior Art

Commercial crude terephthalic acid contains on a weight basis from about 800 p.p.m. to about 7,000 p.p.m. 4-carboxybenzaldehyde and about 200 p.p.m. to about 1,500 p.p.m. p-toluic acid as the main impurities and some crude terephthalic acid also contains lesser amounts, e.g., about 20 to about 200 p.p.m. of yellow-colored aromatic compounds having the structures of benzil, fluorenone or anthraquinone, which are characteristically yellow compounds as impurities resulting from coupling side reactions occurring during the oxidation of p-xylene. These yellow-colored aromatic compounds absorb light in regions of the ultraviolet and visible spectra where terephthalic acid does not absorb significantly. These yellow compounds by virtue of their absorption increase the "optical density" of purified terephthalic acid solutions and, therefore, optical density is used as a measure of the impurities of purified terephthalic acid.

U.S. Pat. No. 3,584,039, issued to Delbert H. Meyer, teaches a feasible, commercially useful method for purification of such commercially available crude terephthalic acid products by treating liquid phase solutions thereof in water at temperatures of 200° C. (392° F.) to 374° C. (705° F.) with hydrogen in the presence of a solid hydrogenation catalyst (e.g., metallic palladium on carbon support) and crystallizing terephthalic acid from catalyst-free liquid phase solutions at temperatures in the range of 50° C. (123° F.) to 150° C. (302° F.). The catalytic hydrogen treatment converts 4-carboxybenzaldehyde to p-toluic acid and decolorizes the terephthalic acid.

British Patent No. 1,152,575 is directed to the development of the Meyer Patent method for its commercial application by providing improved modes of conduct for the entire process from the step of dissolving crude terephthalic acid through the step of crystallizing terephthalic acid from the hydrogen treated aqueous solution. With respect to said crystallization, said British patent teaches the use of solvent evaporation to effect the cooling necessary to precipitate crystalline terephthalic acid, but cautions that conduct of such evaporative cooling should avoid shock cooling of the solution as would occur by instantaneous flash evaporation of solvent because such shock cooling coprecipitates dissolved impurities which contaminate terephthalic acid product. To prevent the contaminating effect of such shock cooling, the British patent teaches that the evaporative cooling should be controlled by evaporation against equilibrium back pressure, for example, by throttling of steam vapor exhaust at the equilibrium pressure. This is in effect a controlled rate evaporative cooling.

U.S. Pat. No. 3,931,305 assumes that the catalytic hydrogen treatment decolorizes the terephthalic acid and that the crystallization train is a means for separating unreacted 4-carboxybenzaldehyde and its hydrogenation product p-toluic acid from the remaining terephthalic acid. The process disclosed in U.S. Pat. No. 3,931,305 has been improved by virtue of a reduction in the O.D. content in excess of 90%, usually about 92%. This has been accomplished via the addition of 100 gm. to 600 gm. of water per 1,000 gm. of terephthalic acid to one or more crystallization zones, each zone being operated at a successively lower temperature. The initial optical density value of 1.183 was changed to a final optical density value of 0.089.

Crystallization by controlled rate evaporative cooling is, according to the above British patent, applied to continuous crystallization conducted in three series-connected stages under the conditions described to effect in 3.4 hours a 150° C. (302° F.) temperature drop from 277° C. (530° F.) initial solution temperature to the third stage temperature of 109° C. (228° F.). This mode of conducting said crystallization which provided an average cooling rate of 1.48° F. per minute was not only inordinately slow but, when applied to aqueous solutions of terephthalic acid of 2,400 p.p.m. p-toluic acid content, also provided a terephthalic acid product containing 1,200 p.p.m. p-toluic acid. Such product would not be acceptable for direct reaction with ethylene glycol for polyester fiber manufacture.

The use of flash solvent evaporation induced crystallization of terephthalic acid from aqueous solution also containing dissolved p-toluic acid in amounts of 500 p.p.m. to 6,000 p.p.m. based on terephthalic acid can, without proper conduct thereof, bring into play the p-toluic acid contamination phenomenon alluded to in the British patent and more generally described in the later United States patent. Such contamination phenomenon is somewhat anomalous because, in spite of the fact that there is retained more than enough solvent water to prevent saturation or supersaturation with respect to p-toluic acid, p-toluic acid nevertheless comes out of solution. Said later United States patent suggests that the contamination phenomenon is in some way dependent on the rate of crystallization and the final temperature of crystallization and product separation and not solely on p-toluic acid concentration in the solution.

U.S. Pat. No. 3,497,552, issued to George P. Olsen, is directed to continuous crystallization of terephthalic acid in the presence of more soluble contaminants wherein water is injected into a large recycle loop for each crystallizer in a series of crystallizers, with crystallizer cooling occurring in the external recycle loop. Crystallization of an organic compound solute from solution is conducted without evaporating or otherwise removing solvent and without shock cooling of the solution of the organic compound solute.

Now there has been developed a process for reducing the optical density of terephthalic acid product, wherein water is added directly to one or more crystallizers in a series of crystallizers.

SUMMARY OF THE INVENTION

A process of producing terephthalic acid having 150 p.p.m. or less p-toluic acid content by weight (i.e., fiber-grade quality terephthalic acid) and whose optical density has been reduced in excess of 90 weight percent from a value of about 1.183 to a value of about 0.089 has been discovered, which process is applicable to aqueous solutions of terephthalic acid having 500 p.p.m. to 6,000 p.p.m. by weight of p-toluic acid and advantageously makes use of substantially instantaneous crystallization of incremental proportions of dissolved terephthalic acid in a small number, at least two, series-connected stirred crystallization zones to which zones about 100 gm. to about 600 gm. of water are added per 1,000 gm. of terephthalic acid. Such continuous crystallization and addition of water to one or more crystallizers can be successfully applied to aqueous solutions substantially saturated with terephthalic acid at temperatures in the range of 204° C. (400° F.) to 288° C. (550° F.), provided that at least the zones operated at temperatures of 191° C. (375° F.) to 149° C. (300° F.) and below, and preferably all the zones are so operated to crystallize decreasing proportions of originally dissolved terephthalic acid.

CROSS-REFERENCES TO RELATED APPLICATION

A process for reducing the optical density of terephthalic acid product in excess of 90% via the addition of water to crystallization zones was disclosed in a prior patent application, U.S. Ser. No. 430,341, now abandoned. In this prior application, the addition of water to the zones was not expressly claimed as being added directly to the zones.

DETAILED DESCRIPTION AND PREFERRED EMBODIMENT

The success of the present inventive process is hereinafter demonstrated.

It is indeed surprising that relatively small amounts of water added to one or more crystallizers can have a significant effect on the reduction of optical density.

As mentioned hereinabove, various organic impurities may contaminate the terephthalic acid product. Among these is p-toluic acid, a primary impurity. Contamination by such impurities affects the optical density of the terephthalic acid product. The addition of water to one or more crystallizers during the process greatly reduces the optical density of the terephthalic acid product. Apparently, sufficient amounts of the impurities are removed from the product, resulting in substantial decreases of the optical density.

According to the present invention, there is provided a process for reducing the optical density of terephthalic acid product in excess of 90 percent from a liquid aqueous solution which is substantially saturated with terephthalic acid and which comprises about 500 p.p.m. to about 6,000 p.p.m. of p-toluic acid at a temperature within the range of about 204° C. (400° F.) to about 288° C. (550° F.), which process comprises, after continuously charging said liquid solution to the first zone in a series of two or more stirred crystallization zones which use flash evaporation of water, adding directly to at least one of said zones water in an amount within the range of about 100 gm. to about 600 gm. of water per 1,000 gm. of terephthalic acid, each of said zones being operated at a successively lower temperature wherein at least the last zone is operated at a temperature within and below the range of about 191° C. (375° F.) to about 149° C. (300° F.) crystallizing decreasing proportions of originally dissolved terephthalic acid, and removing the flash evaporated water from each of said zones while retaining temperature of recovery of terephthalic acid product the same as the temperature of the last zone.

The choice of the real and effective number of series-connected stirred crystallization zones using flash evaporation of water is associated with the concentration of p-toluic acid based on terephthalic acid and not on the p-toluic acid concentration in the solution fed to any other zone, and since crystallization of each incremental amount of terephthalic acid is substantially instantaneous, not on any rate dependent technique for effecting terephthalic acid crystallization. For such initially dissolved terephthalic acid having 500 p.p.m. to 6,000 p.p.m. of p-toluic acid by weight based on terephthalic acid, the number of such flash evaporations of solvent in series, in general, will not exceed a total of eight stirred crystallization zones. For example, two such zones are adequate for 500 p.p.m. to 1,000 p.p.m. p-toluic acid, three such zones are adequate for 500 p.p.m. to 2,500 p.p.m. p-toluic acid, four such zones are adequate for 1,500 p.p.m. to 4,000 p.p.m. p-toluic acid, and five to eight zones are adequate for 2,000 p.p.m. to 6,000 p.p.m. p-toluic acid based on terephthalic acid initially in solution. Water addition can be made to each crystallizer or at least to one of the crystallizers. In systems using crystallizers advantageously, water is added to the acid through the fifth crystallizer. However, those number of zones associated with p-toluic acid concentrations on terephthalic acid are not the only number which can be successfully used for, as will be hereafter demonstrated, fiber-grade quality terephthalic acid (i.e., not more than about 150 p.p.m. p-toluic acid) can be recovered using 3 to 6 stirred crystallization zones when the p-toluic acid content on terephthalic acid is 1,500 p.p.m. to 6,000 p.p.m. For said 1,500 p.p.m. to 6,000 p.p.m. p-toluic acid content terephthalic acid, it is preferred to use 3 to 6 zones of solvent flash evaporation and it is preferred to add the water to the last three crystallizers. It is also preferred, from the standpoint of capital investment cost for commercial operation of the present inventive continuous process, to use 2 to 6 zones of flash solvent evaporation for initial p-toluic acid concentrations on terephthalic acid in the range of 500 p.p.m. to 6,000 p.p.m. by weight.

For the conduct of each of the 2 to 8, preferably 3 to 6, zones of flash solvent evaporation each incremental amount of original water evaporated is not returned to any stage of the process. Selection of the operating temperature for each flash solvent evaporation in the series of 2 to 8, preferably 3 to 6, stirred crystallization zones can be judiciously made from a plot of terephthalic acid saturation concentration against temperature so that the temperature profile of the entire process reasonably follows said plot. The illustrative examples hereinafter presented will provide a number of such temperature profiles which can be followed to obtain the same results indicated or which can serve as guidance for selecting different temperature profiles for operating with solutions having concentrations of p-toluic acid differing from those illustrated but within the range of 500 p.p.m. to 6,000 p.p.m. by weight on terephthalic acid.

Substantial flexibility of operation of the present inventive process is possible with respect to the initial aqueous solution feed contents of not only dissolved terephthalic acid and its p-toluic acid content within the range of 500 p.p.m. to 6,000 p.p.m. by weight, but also with respect to selection of a number of stirred crystallization zones and even the final quality of terephthalic acid product. The temperature-dependent p-toluic acid rejection becomes of importance after a temperature in the range of 191° C. (375° F.) to 149° C. (300° F.) has been reached. The increments of originally dissolved terephthalic acid crystallized in each such zone can be substantial until said 191° C.-to-149° C. temperature is reached and thereafter each crystallized increment of originally dissolved terephthalic acid should be decreasingly smaller. The water should be added to these last crystallization stages to reduce the optical density by more than ninety percent; however, each of such smaller increments is not restricted to a critically limiting single fraction of originally dissolved terephthalic acid. The temperature dependent phenomenon and need to diminish the increments of terephthalic acid crystallized below said 191° C.-to-149° C. temperature range indicates flexibility rather than inflexibility of the process operation.

In general, the key factor to selecting the temperature profile for the crystallization zones from 191° C. (375° F.) to 149° C. (300° F.) and below involves the selection of each zone temperature so that each increment of terephthalic acid crystallized in each stage is progressively smaller than the increment of the preceding zone. This will not only minimize the proportion of terephthalic acid crystallized below the 171° C. (340° F.)-to-160° C. (320° F.) range, but also minimize p-toluic acid contamination.

The optical density is measured according to the procedure set forth hereinbelow.

TEREPHTHALIC ACID SAMPLES

A terephthalic acid sample (3.1 to 3.3 gm.) was dissolved in 50 ml. 4N NH$_4$OH. The absorbance of the resulting solution was measured at 340 nm with a Perkin Elmer 552, 550, 200 or equivalent spectrophotometer using a square silica cuvette 5 cm. in length. All measurements were expressed for a 50 mm. pathlength and a 6.5% terephthalic acid solution (standard conditions) as follows:

$$O.D._{340} = A_{340} \frac{50 \text{ mm.}}{X_l} \frac{3.25 \text{ gm.}}{X_S}$$

Where, $O.D._{340}$ = optical density at 340 nm.
Sample
$A_{340}$ = absorbance of the sample at 340 nm.
$l$ = pathlength of cuvette in mm.
$X_S$ = weight of sample in gm.

FEED SLURRY SAMPLES

A sample of PTA slurry containing approximately 3 gm. of solids was dissolved in 50 ml. 4N NH$_4$OH. The absorbance of the resulting solution was measured at 340 nm as above. In addition, 1 ml. of the solution was diluted to 500 ml. with deionized water and the absorbance of the new solution measured at 290 nm. This measurement detected terephthalic acid and was used to correct the absorbance at 340 nm to the standard terephthalic acid conditions.

The measured absorbance at 290 nm was used to determine the grams of terephthalic acid present in the samples as follows:

Sample
$X_S = S_c \times A_{290}$ where;
$S_c$ = slope of $A_{290}$ calibration curve
Sample
$A_{290}$ = absorbance of the diluted sample at 290 nm.

The correction for the absorbance at 340 nm to standard conditions was the same as that given for terephthalic acid samples using the grams of terephthalic acid calculated above for $X_S$.

COMPARATIVE EXAMPLE 1

An aqueous solution containing 20 weight percent terephthalic acid (25 pounds terephthalic acid per 100 pounds of water) and 2,500 p.p.m. p-toluic acid based on terephthalic acid at a temperature of 269° C. (515° F.) and 800 pounds per square inch absolute (psia) pressure was used as feed into a stirred crystallization zone operated at a temperature of 149° C. (300° F.) and 67 psia. Such solution was charged continuously to said zone through a flow control valve immediately adjacent to the inlet port of the crystallizer. The steam generated by the flash evaporation of water from 269° C. (515° F.) to 149° C. (300° F.) was withdrawn from the crystallizer, condensed and discarded. The resulting suspension of terephthalic acid crystals was centrifuged at a temperature of 149° C. (300° F.) and a pressure of 67 psia. The recovered solid crystalline terephthalic acid was dried. The dry terephthalic product obtained by such operation was found to contain about 1,200 p.p.m. by weight of p-toluic acid and provided an optical density of 1.6.

COMPARATIVE EXAMPLE 2

The above process was repeated except the p-toluic acid content of dissolved terephthalic acid was 500 p.p.m. by weight. The recovered dry terephthalic acid product produced by such operation was found to contain about 250 p.p.m. of p-toluic acid by weight and had an optical density of 0.8.

EXAMPLES 1 to 4

The above-described feed solution was continuously charged to the first stirred zone in a system comprising five stirred crystallization zones. The magma (crystals plus solution) produced in each stirred zone was charged sequentially to each of the following stirred zones. The magma produced in the last zone was charged continuously to the centrifuge. In all operations, the last stirred zone and the centrifuge were operated at the temperature of 149° C. (300° F.) and pressure of 67 psia.

The temperature (T,°C.) and pressure (P, psia) for each crystallization step and the centrifuge for conduct of the five series-connected stirred zone operation are indicated hereinafter in Table 1.

It is to be emphasized that, while the data were obtained from a system comprising five crystallization steps, similar results would be obtained from systems employing 3, 4, or 6 multi-zone continuous flash evaporation crystallizations.

TABLE 1

CONTINUOUS FLASH SOLVENT EVAPORATION, TA CRYSTALLIZATION
Aqueous Feed Solution 26.5 Weight Percent
Terephthalic Acid (TA) with 750 p.p.m. p-Toluic Acid at

|  | Example 1 | Example 2 | Example 3 | Example 4 |
|---|---|---|---|---|
| Reactor temperature, °C. | 282 | 282 | 282 | 282 |
| Feed slurry, O.D.[1] | 0.850 | 1.183 | 1.270 | 1.042 |
| Water added, gm. per 1,000 gm. TA | 133.8 1st crystallizer | 131.4 1st crystallizer 346.9 4th crystallizer | 151 3rd crystallizer 187 4th crystallizer | 251.6 4th crystallizer 254 5th crystallizer |
| Location |  |  |  |  |
| 1st crystallizer temperature, °C. | 238 | 238 | 238 | 238 |
| 2nd crystallizer temperature, °C. | 216 | 216 | 216 | 216 |
| 3rd crystallizer temperature, °C. | 188 | 188 | 188 | 188 |
| 4th crystallizer temperature, °C. | 166 | 166 | 166 | 166 |
| 5th crystallizer temperature, °C. | 149 | 149 | 149 | 149 |
| Temperature of water addition, °C. | 1st crystallizer 149 | 1st crystallizer 149 4th crystallizer 149 | 3rd crystallizer 160 4th crystallizer 160 | 4th crystallizer 151 5th crystallizer 151 |
| Product O.D.[1] | 0.080 | 0.089 | 0.10 | 0.08 |
| % O.D.[1] Reduction | 90.5 | 92.6 | 91.1 | 92.3 |
| Total water added, gm. per 1,000 gm. TA | 133.8 | 478.3 | 337.9 | 506.0 |

[1] O.D. = optical density

That which is claimed is:

1. A process for reducing the optical density of terephthalic acid product in excess of 90 percent from a liquid aqueous solution which is substantially saturated with terephthalic acid and which comprises about 500 p.p.m. to about 6,000 p.p.m. of p-toluic acid at a temperature within the range of about 204° C. to about 288° C., which process comprises, after continuously charging said liquid solution to the first zone in a series of two or more stirred crystallization zones which use flash evaporation of water, adding directly to at least one of said zones water in an amount within the range of about 100 gm to about 600 gm. of water per 1,000 gm. of terephthalic acid, each of said zones being operated at a successively lower temperature wherein at least the last zone is operated at a temperature within and below the range of about 191° C. to about 149° C. crystallizing decreasing proportions of originally dissolved terephthalic acid, and removing the flash evaporated water from each of said zones while retaining temperature of recovery of terephthalic acid product the same as the temperature of the last zone.

2. The process of claim 1, wherein the number of said zones is within the range of about 2 to about 8.

3. The process of claim 1, wherein the temperature of said last zone is within the range of about 171° C. to about 149° C.

4. The process of claim 2, wherein the number of said zones is within the range of about 3 to about 6.

5. The process of claim 4, wherein there are at least four zones in said series of stirred crystallization zones and said adding of water is carried out to the third and fourth zones in said series of stirred crystallization zones.

6. The process of claim 4, wherein the number of said zones is 6.

7. The process of claim 4, wherein the number of said zones is 5 and said adding of water is being carried out to the fourth and fifth zones of said series of stirred crystallization zones.

8. The process of claim 5, wherein the temperature of said last zone is within the range of about 171° C. to about 149° C.

9. The process of claim 6, wherein said adding of water is being carried out to the fourth, fifth, and sixth zones in said series of stirred crystallization zones.

10. The process of claim 7, wherein the temperature of said last zone is within the range of about 171° C. to about 149° C.

11. The process of claim 6, wherein the temperature of said last zone is within the range of about 171° C. to about 149° C.

12. The process of claim 9, wherein the temperature of said last zone is within the range of about 171° C. to about 149° C.

* * * * *